(12) United States Patent
Peglion et al.

(10) Patent No.: US 8,110,701 B2
(45) Date of Patent: Feb. 7, 2012

(54) PROCESS FOR THE PREPARATION OF FUNCTIONALISED BENZOCYCLOBUTENES, AND APPLICATION IN THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Olivier Baudoin, Meyzieu (FR); Nicolas Audic, Amiens (FR); Manon Chaumontet, Toulouse (FR); Riccardo Piccardi, Antony (FR)

(73) Assignees: Les Laboratoires Servier, Suresnes Cedex (FR); Centre National de la Recherche Scientifique, Paris Cedex (FR); Universite Claude Bernard Lyon 1, Villeurbanne Cedex (FR)

( * ) Notice: Subject to any disclaimer, the term of this patent is extended or adjusted under 35 U.S.C. 154(b) by 383 days.

(21) Appl. No.: 12/460,208

(22) Filed: Jul. 15, 2009

(65) Prior Publication Data

US 2010/0016580 A1    Jan. 21, 2010

(30) Foreign Application Priority Data

Jul. 17, 2008    (FR) ..................................... 08 04061

(51) Int. Cl.
*C07C 69/76*    (2006.01)
(52) U.S. Cl. ...................................................... 560/101
(58) Field of Classification Search .................. None
See application file for complete search history.

(56) References Cited

FOREIGN PATENT DOCUMENTS

EP    0534859    3/1993

OTHER PUBLICATIONS

Chaumontet et al., Journal of the American Chemical Society (2008), 130(45), 15157-15166.*
Chaumontet et al., Journal of Organic Chemistry (2009), 74(4), 1774-1776.*

Olivier Baudoin Audrey Herrbach, et al., "The Palladium-catalyzed C-H activation of benzylic gem-Dialkyl groups" Angewandte Chemie, vol. 42, No. 46, p. 5736-5740, 2003.
T. Kametani, et al., "Studies of the syntheses of heterocyclic compounds" TETRAHDRON, vol. 29, p. 73-76, 1973.
Manon Chaumontet, et al., "Synthesis of Benzocyclobutenes by palladium-catalyzed C-H activation of methyl groups: Method and mechanistic study" Journal of the American Chemical Society, vol. 130, No. 45, p. 1515-15166, Oct. 18, 2008.
French Preliminary Search Report for FR0804061 of Mar. 10, 2009.

* cited by examiner

*Primary Examiner* — Karl J Puttlitz
(74) *Attorney, Agent, or Firm* — Hueschen and Sage

(57) ABSTRACT

Process for the preparation of compounds of formula (IV):

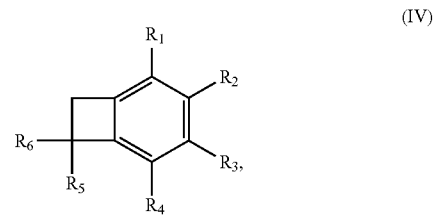

wherein $R_1$, $R_2$, $R_3$ and $R_4$, which may be identical or different, each represent a hydrogen atom, a linear or branched ($C_1$-$C_6$)alkyl group, a linear or branched ($C_1$-$C_6$)alkoxy group, a fluorine atom, a chlorine atom, a protected amine group, a protected hydroxyl group, an alkoxycarbonyl group in which the alkoxy group is linear or branched ($C_1$-$C_6$), or a $CF_3$ group, or $R_1$=$R_4$=H and $R_2$ and $R_3$ together with the carbon atoms carrying them form a 1,3-dioxolane group,
$R_5$ represents a saturated or unsaturated, linear or branched ($C_1$-$C_6$)alkyl group, a linear or branched ($C_1$-$C_6$)hydroxyalkyl group in which the hydroxyl function is protected, or a $CO_2R_7$ group in which $R_7$ is a linear or branched ($C_1$-$C_6$)alkyl group,
$R_6$ represents a cyano group or a $CO_2R_8$ group in which $R_8$ is a linear or branched ($C_1$-$C_6$)-alkyl group.
Application in the synthesis of ivabradine, addition salts thereof with a pharmaceutically acceptable acid and hydrates thereof.

7 Claims, No Drawings

PROCESS FOR THE PREPARATION OF FUNCTIONALISED BENZOCYCLOBUTENES, AND APPLICATION IN THE SYNTHESIS OF IVABRADINE AND ADDITION SALTS THEREOF WITH A PHARMACEUTICALLY ACCEPTABLE ACID

The present invention relates to a process for the preparation of functionalised benzocyclobutenes, and to their application in the synthesis of ivabradine, addition salts thereof with a pharmaceutically acceptable acid and hydrates thereof.

Ivabradine of formula (I):

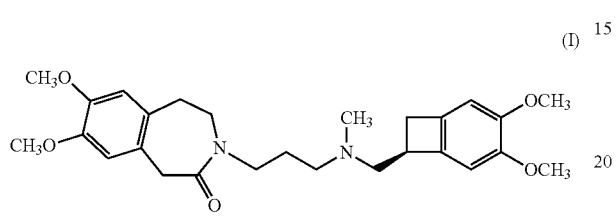

(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, and also addition salts thereof with a pharmaceutically acceptable acid, and more especially the hydrochloride thereof, have very valuable pharmacological and therapeutic properties, especially bradycardic properties, which render those compounds useful in the treatment or prevention of various clinical situations of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the synthesis of ivabradine using as starting material a compound of formula (II):

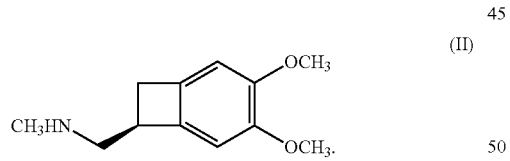

(II)

The compound of formula (II) is obtained by resolving, with the aid of camphosulphonic acid, the compound of formula (III):

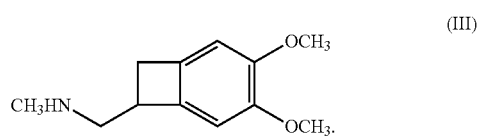

(III)

The compound of formula (II) is an important intermediate in the synthesis of ivabradine.

The present invention relates to a process for the preparation of functionalised benzocyclobutenes and to their application in the synthesis of ivabradine, addition salts thereof with a pharmaceutically acceptable acid and hydrates thereof via the compound of formula (II).

The preparation of functionalised benzocyclobutenes has been described in *Angewandte Chemie, International Edition* 2003, 42, 5736-5740. This publication describes the possibility of applying $C(sp^3)$-H bond activation to the preparation of functionalised benzocyclobutenes using a palladium catalyst system.

More specifically, the present invention relates to a process for the preparation of the compounds of formula (IV):

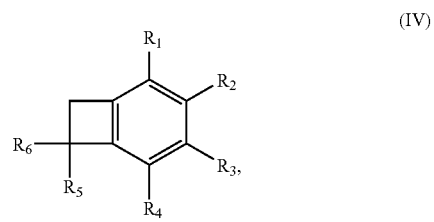

(IV)

wherein $R_1$, $R_2$, $R_3$ and $R_4$, which may be identical or different, each represent a hydrogen atom, a linear or branched $(C_1-C_6)$alkyl group, a linear or branched $(C_1-C_6)$alkoxy group, a fluorine atom, a chlorine atom, a protected amine group, a protected hydroxyl group, an alkoxycarbonyl group in which the alkoxy group is linear or branched $(C_1-C_6)$, or a $CF_3$ group, or $R_1=R_4=H$ and $R_2$ and $R_3$ together with the carbon atoms carrying them form a 1,3-dioxolane group, $R_5$ represents a saturated or unsaturated, linear or branched $(C_1-C_6)$alkyl group, a linear or branched $(C_1-C_6)$hydroxyalkyl group in which the hydroxyl function is protected, or a $CO_2R_7$ group in which $R_7$ is a linear or branched $(C_1-C_6)$alkyl group, $R_6$ represents a cyano group or a $CO_2R_8$ group in which $R_8$ is a linear or branched $(C_1-C_6)$-alkyl group, which process is characterised in that a compound of formula (V):

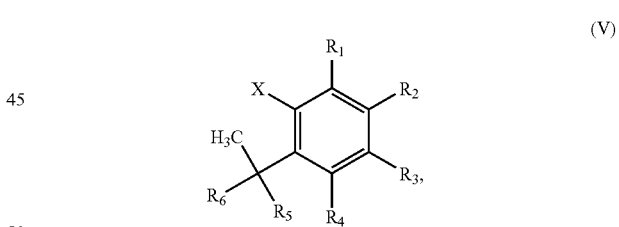

(V)

wherein $R_1$, $R_2$, $R_3$, $R_4$, $R_5$, $R_6$ are as defined hereinbefore and X represents a halogen atom, preferably a bromine atom, or a triflate group, is subjected to a cyclisation reaction in the presence of a catalyst/ligand system comprising a palladium catalyst and an organic phosphine selected from tri-tert-butylphosphine, 2-biphenyl-di-tert-butylphosphine, 1,2,3,4,5-pentaphenyl-1'-(di-tert-butylphosphino)-ferrocene and tris(4-methoxy-2-methylphenyl)phosphine, or a phosphonium salt of the said phosphines, in the presence of a base, in an organic solvent.

Protected hydroxyl group or protected hydroxyl function means a hydroxyl function substituted by a protecting group customary for that function. Among those protecting groups there may be mentioned, without implying any limitation, silyl-containing groups such as triisopropylsilyl and tert-butyldimethylsilyl, and the groups tetrahydropyran, benzyl, para-methoxybenzyl, trityl, acetyl and pivaloyl.

A protected amine group means an amine function substituted by a protecting group customary for that function. Among those protecting groups there may be mentioned, without implying any limitation, the groups nosyl, tosyl, mesyl, acetyl, tert-butoxycarbonyl, benzyl and phthalimide.

Among the palladium catalyst that can be used there may be mentioned, without implying any limitation, $Pd(OAc)_2$, $Pd(dba)_2$, $Pd_2(dba)_3$, $PdCl_2$, $PdCl_2(CH_3CN)_2$, $PdBr_2$, or trans-di-(μ-acetate)bis[o-(di-o-tolylphosphine)benzyl]dipalladium (Herrmann's catalyst).

The palladium catalyst preferably used is $Pd(OAc)_2$.

The organic phosphine preferably used is tri-tert-butylphosphine.

Among the phosphonium salts that can be used there may be mentioned, without implying any limitation, phosphonium tetrafluoroborates, hexafluorophosphates and hexafluoroantimonates.

The phosphonium salt preferably used is tri-tert-butylphosphonium tetrafluoroborate.

Among the bases that can be used there may be mentioned, without implying any limitation, $K_2CO_3$, $Cs_2CO_3$, $Na_2CO_3$, $K_3PO_4$, $KHCO_3$, $t\text{-}BuCO_2Na$, $t\text{-}BuCO_2K$ and $t\text{-}BuCO_2Cs$.

The base preferably used is $K_2CO_3$.

Among the solvents that can be used there may be mentioned, without implying any limitation, DMF, N,N-dimethylacetamide, N-methylpyrrolidine, xylene and mesitylene.

The solvent preferably used is DMF.

The temperature of the reaction is preferably from 100° C. to 150° C.

According to a preferred embodiment, the present invention relates to a process for the preparation of compounds of formula (IVa), particular cases of the compounds of formula (IV) wherein $R_5=CO_2R_7$ and $R_6=CO_2R_8$:

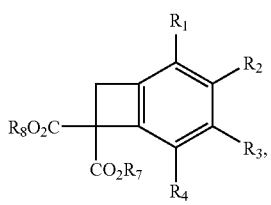

(IVa)

wherein $R_1$, $R_2$, $R_3$, $R_4$, $R_7$ and $R_8$ are as defined hereinbefore, starting from compounds of formula (Va), particular cases of the compounds of formula (V) wherein $R_5=CO_2R_7$ and $R_6=CO_2R_8$:

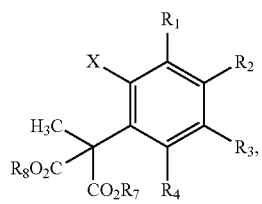

(Va)

wherein $R_1$, $R_2$, $R_3$, $R_4$, $R_7$, $R_8$ and X are as defined hereinbefore.

According to another preferred embodiment, the present invention relates to a process for the preparation of compounds of formula (IVb), particular cases of the compounds of formula (IVa) wherein $R=R_4=H$ and $R_2=R_3=OCH_3$:

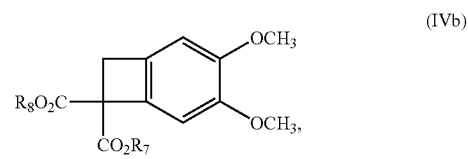

(IVb)

wherein $R_7$ and $R_8$ are as defined hereinbefore, starting from compounds of formula (Vb), particular cases of the compounds of formula (Va) wherein $R=R_4=H$ and $R_2=R_3=OCH_3$:

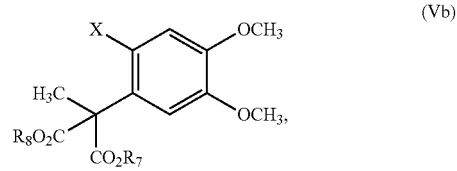

(Vb)

wherein $R_7$, $R_8$ and X are as defined hereinbefore.

The compounds of formula (IVa) obtained according to the process of the invention can lead to compounds of formula (VIa):

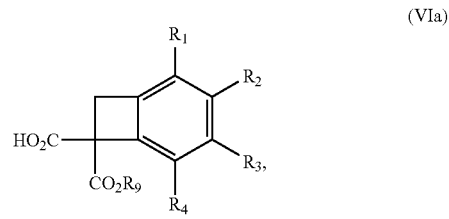

(VIa)

wherein $R_1$, $R_2$, $R_3$ and $R_4$ are as defined hereinbefore and $R_9$ is a linear or branched $(C_1\text{-}C_6)$alkyl group, by an ester saponification or hydrolysis reaction, then the compounds of formula (VIa) lead to compounds of formula (VIIa):

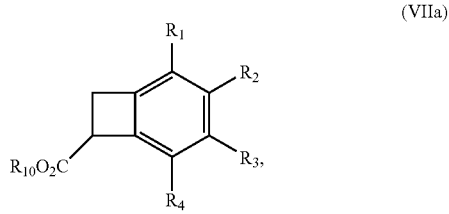

(VIIa)

wherein $R_1$, $R_2$, $R_3$ and $R_4$ are as defined hereinbefore and $R_{10}$ is a hydrogen atom or a linear or branched $(C_1\text{-}C_6)$ alkyl group, by a decarboxylation reaction.

The hydrolysis or the saponification of an ester function of the compounds of formula (IVb) results in compounds of formula (VIb), particular cases of the compounds of formula (VIa) wherein $R_1=R_4=H$ and $R_2=R_3=OCH_3$:

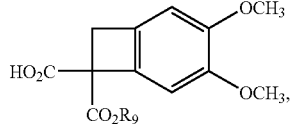

wherein $R_9$ is as defined hereinbefore.

The decarboxylation of the compounds of formula (VIb) then results in compounds of formula (VIIb), particular cases of the compounds of formula (VIIa) wherein $R_1=R_4=H$ and $R_2=R_3=OCH_3$:

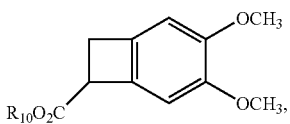

wherein $R_{10}$ is as defined hereinbefore.

The compounds of formula (VIIb) obtained according to the process of the invention are useful in the synthesis of ivabradine, addition salts thereof with a pharmaceutically acceptable acid and hydrates thereof.

By way of example, their reaction with methylamine results in the compound of formula (VIII):

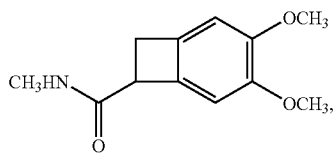

the reduction of which results in the compound of formula (III):

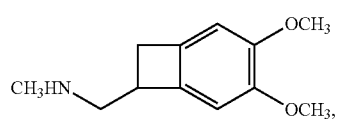

the resolution of which, using camphosulphonic acid, results in the compound of formula (II):

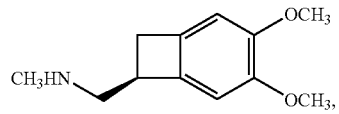

which is converted into ivabradine of formula (I)

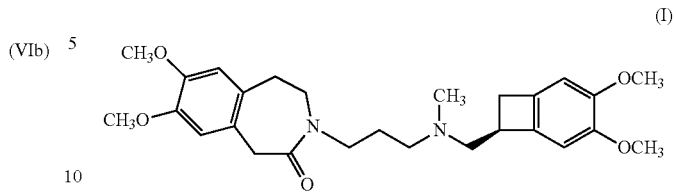

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, which may optionally be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into its hydrates.

Among the methods known for carrying out the conversion of the compound of formula (II) to ivabradine, those described in the European patent specifications EP 0 534 859 and EP 1 589 005 may be mentioned.

Obtaining compounds of formula (IVb) in good yields is thus especially useful in the synthesis of ivabradine, addition salts thereof with a pharmaceutically acceptable acid and hydrates thereof.

The compounds of formula (IVa), which are particular cases of the compounds of formula (IV) wherein $R_5=CO_2R_7$ and $R_6=CO_2R_8$, and also the compounds of formula (VIb), as well as the compounds of formula (VIIc), which are particular cases of the compounds of formula (VIIb) wherein $R_{10}$ represents a linear or branched $(C_1-C_6)$alkyl group, are new products which are useful as synthesis intermediates in the chemical or pharmaceutical industry, especially in the synthesis of ivabradine, addition salts thereof with a pharmaceutically acceptable acid and hydrates thereof and, as such, constitute an integral part of the present invention.

List of the Abbreviations Used:
dba: dibenzylidene acetone
DMF: N,N-dimethylformamide
DMSO: dimethyl sulphoxide
eq.: equivalent
THF: tetrahydrofuran The Examples hereinbelow illustrate the invention.

General Procedure A for the Formation of Benzocyclobutenes by C—H Bond Activation Introduce aryl bromide (1 mmol), $Pd(OAc)_2$ (0.1 eq.), $P(t-Bu)_3 \cdot HBF_4$ (0.2 eq.) and anhydrous $K_2CO_3$ (1.3 eq.) into a dry and hermetically sealable Schlenk tube provided with a bar magnet. The Schlenk tube is purged and placed under argon. 4 ml of anhydrous DMF are added under argon, and the Schlenk tube is hermetically sealed and then subjected to stirring in an oil bath preheated to 140° C. until complete disappearance of the aryl bromide in GC/MS. After returning to ambient temperature, the reaction mixture is diluted with diethyl ether and filtered over Celite®. The organic solution is washed with saturated aqueous NaCl solution and dried over $MgSO_4$ and the residual solvent is evaporated off under reduced pressure. The crude reaction product is purified by flash chromatography to yield the benzocyclobutene.

General Procedure B for the Formation of Benzocyclobutenes by C—H Bond Activation Introduce aryl bromide (1 mmol), $Pd_2(dba)_3$ (0.05 eq.), $P(t-Bu)_3 \cdot HBF_4$ (0.1 eq.) and anhydrous $K_2CO_3$ (1.3 eq.) into a dry and hermetically sealable Schlenk tube provided with a bar magnet. The Schlenk tube is purged and placed under argon. 4 ml of anhydrous DMF are added under argon, and the Schlenk tube is hermetically sealed and then subjected to stirring in an oil bath preheated to 120° C. until complete disappearance of the aryl bromide in GC/MS. After returning to ambient temperature, the reaction mixture is diluted with diethyl ether and filtered over Celite®. The organic solution is extracted with saturated aqueous NaCl solution and dried over $MgSO_4$ and the residual solvent is evaporated off under reduced pressure. The crude reaction product is purified by flash chromatography to yield the benzocyclobutene.

EXAMPLE 1

Dimethyl 7-methylbicyclo[4.2.0]octa-1,3,5-triene-3,7-dicarboxylate

Following general procedure A and using methyl 3-bromo-4-(2-methoxy-1,1-dimethyl-2-oxoethyl)benzoate as starting material, the title compound is obtained in a yield of 92%.

IR (film): $\nu$=2952, 1714, 1433, 1275, 1146, 1079, 768 $cm^{-1}$.

EXAMPLE 2

Methyl 7-methyl-4-(trifluoromethyl)bicyclo[4.2.0]octa-1,3,5-triene-7-carboxylate Following general procedure A and using methyl 2-[2-bromo-5-(trifluoromethyl)phenyl]-2-methylpropanoate as starting material, the title compound is obtained in a yield of 81%.

IR (film): $\nu$=2955, 1731, 1315, 1143, 1113, 826, 685 $cm^{-1}$.

EXAMPLE 3

7-Isopropylbicyclo[4.2.0]octa-1,3,5-triene-7-carbonitrile

Following general procedure A and using 2-(2-bromophenyl)-2,3-dimethylbutanenitrile as starting material, the title compound is obtained in a yield of 72%.

IR (film): $\nu$=2964, 1458, 748, 715 $cm^{-1}$.

EXAMPLE 4

Dimethyl 3-methylbicyclo[4.2.0]octa-1,3,5-triene-7,7-dicarboxylate

Following general procedure A and using dimethyl 2-(2-bromo-4-methylphenyl)-2-methylmalonate as starting material, the title compound is obtained in a yield of 87%.

IR (film): $\nu$=2952, 1731 $cm^{-1}$.

EXAMPLE 5

Dimethyl 3,4-dimethoxybicyclo[4.2.0]octa-1,3,5-triene-7,7-dicarboxylate

The title compound is obtained according to general procedure A using dimethyl 2-(2-bromo-4,5-dimethoxyphenyl)-2-methylmalonate as starting material.

IR (pure): $\nu$=3007, 2960, 1730, 1591, 1239, 1116, 1090, 878, 758 $cm^{-1}$.

EXAMPLE 6 tert-Butyl methyl 3,4-dimethoxybicyclo[4.2.0]octa-1,3,5-triene-7,7-dicarboxylate Following general procedure A and using tert-butyl methyl 2-(2-bromo-4,5-dimethoxyphenyl)-2-methylmalonate as starting material, the title compound is obtained in a yield of 69%.

IR (pure): $\nu$=2977, 2936, 1728, 1591, 1464, 1249, 1115, 840 $cm^{-1}$.

EXAMPLE 7

Methyl 7-{4-[(triisopropylsilyl)oxy]butyl}bicyclo[4.2.0]octa-1,3,5-triene-7-carboxylate Following general procedure A and using methyl 2-(2-bromophenyl)-2-methyl-6-[(triisopropylsilyl)oxy]hexanoate as starting material, the title compound is obtained in a yield of 82%.

IR (film): $\nu$=2940, 2863, 1731, 1457, 1253, 1103, 881, 678 $cm^{-1}$.

EXAMPLE 8

Methyl 7-methylbicyclo[4.2.0]octa-1,3,5-triene-7-carboxylate

Following general procedure B and using methyl 2-(2-bromophenyl)-2-methylpropanoate as starting material, the title compound is obtained in a yield of 81%.

IR (pure): $\nu$=2972, 2952, 2930, 1729, 1457, 1433, 1277, 1140, 740, 711 $cm^{-1}$.

EXAMPLE 9

(R,S)-3,4-Dimethoxybicyclo[4.2.0]octa-1,3,5-triene-7-carboxylic acid 638 mg (2.28 mmol) of dimethyl 3,4-dimethoxybicyclo[4.2.0]octa-1,3,5-triene-7,7-dicarboxylate obtained in Example 5 are dissolved in 18 ml of DMSO and 445 mg (6.84 mmol) of KCN are added in one go. The mixture is stirred under an argon atmosphere at 130° C. for 12 h. After returning to ambient temperature, 25 ml of aqueous 1N HCl solution and 20 ml of diethyl ether are cautiously added to the reaction mixture (ATTENTION: HCN formation) and the mixture is stirred for 1 h. The organic phase is washed with aqueous 1N NaOH solution (3×10 ml). The aqueous phases are combined, then acidified to pH 2 using aqueous 6N HCl solution at ambient temperature and extracted with diethyl ether (3×15 ml). The organic phases are dried over $MgSO_4$ and the residual solvents are evaporated off under reduced pressure. The crude reaction product is purified by flash chromatography (hexane/ethyl acetate: 85/15) to yield the title compound.

IR (pure): $\nu$=3227, 2842, 2835, 1725, 1593, 1486, 1302, 1160, 1140, 970, 753 $cm^{-1}$.

EXAMPLE 10

Methyl (R,S)-3,4-dimethoxybicyclo[4.2.0]octa-1,3,5-triene-7-carboxylate 424 mg (1.31 mmol) of tert-butyl methyl 3,4-dimethoxybicyclo[4.2.0]octa-1,3,5-triene-7,7-dicarboxylate obtained in Example 6 are dissolved in 2.1 ml of trifluoroacetic acid (99%) and the mixture is refluxed for 1.5 h. After returning to ambient temperature, the mixture is evaporated under reduced pressure to yield the monocarboxylic acid methyl monoester.

The crude compound is dissolved in 4.34 ml of a 30:1 DMF/pyridine mixture and the solution is heated at 120° C. for 2 h under an argon atmosphere and then brought to ambient temperature. The reaction mixture is hydrolysed with saturated aqueous $NH_4Cl$ solution and the aqueous phase is extracted with ethyl acetate (3×10 ml). The organic phases are combined, washed with saturated aqueous NaCl solution (20 ml), dried over $MgSO_4$ and evaporated under reduced pressure. The crude reaction product is purified by flash chromatography (hexane/AcOEt: 8/2) to yield the title product.

IR (pure): ν=2950, 2834, 1729, 1464, 1207, 1068, 729 $cm^{-1}$.

EXAMPLE 11

(R,S)-3,4-Dimethoxy-N-methylbicyclo[4.2.0]octa-1,3,5-triene-7-carboxamide 0.05 ml of sulphuric acid (d=1.83) is added to a solution of 2.5 g (12 mmol) of (R,S)-3,4-dimethoxybicyclo[4.2.0]octa-1,3,5-triene-7-carboxylic acid obtained in Example 9 in 40 ml of methanol. The mixture is refluxed for 2 h and then cooled to 10° C. 40 ml of a 40% solution of methylamine in water are added in the course of 15 min. and the mixture is stirred for 2 h. The methanol is evaporated off under reduced pressure and 40 ml of water are added. After extraction with $CH_2Cl_2$, the combined organic phases are washed in succession with water, 1N HCl and saturated NaCl solution and then dried over $MgSO_4$.

After evaporating off the solvents under reduced pressure, 2.2 g of the title product are obtained in the form of a beige solid (Yield: 83%).

Melting point: 142-147° C.

EXAMPLE 12

(R,S)-1-(3,4-Dimethoxybicyclo[4.2.0]octa-1,3,5-trien-7-yl)-N-methyl-methanamine hydrochloride 20 ml of a molar solution of $BH_3$ in THF are added at ambient temperature to a mixture of 2.2 g (10 mmol) of the product obtained in Example 11 in 45 ml of THF. After stirring for 1 h, 10 ml of the solution of $BH_3$ in THF are added. After stirring overnight at ambient temperature, 20 ml of ethanol are added dropwise and the mixture is stirred until the evolution of gas ceases (about 1 h). 20 ml of a solution of HCl in ethanol are then added dropwise. After stirring for 4 h, the precipitate obtained (1.2 g of the title product) is filtered off. The filtrate is concentrated and a further 0.65 g of title product is obtained by solidifying in an 80:20 AcOEt/ethanol mixture.

The two precipitates are combined to yield 1.85 g of the title product (Yield 77%).

Melting point: 174-177° C.

The invention claimed is:

1. A process for the preparation of a compound selected from those of formula (VIIa):

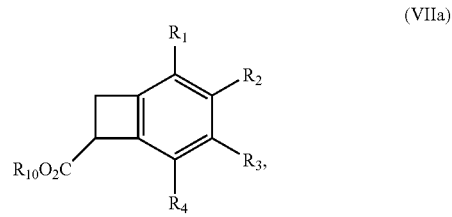

(VIIa)

wherein $R_1$, $R_2$, $R_3$ and $R_4$, which may be identical or different, each represent a hydrogen atom, a linear or branched ($C_1$-$C_6$)alkyl group, a linear or branched ($C_1$-$C_6$)alkoxy group, a fluorine atom, a chlorine atom, a protected amine group, a protected hydroxyl group, an alkoxycarbonyl group in which the alkoxy group is linear or branched ($C_1$-$C_6$), or a $CF_3$ group, or $R_1$ and $R_4$ represent hydrogen and $R_2$ and $R_3$ together with the carbon atoms carrying them form a 1,3-dioxolane group, and $R_{10}$ represents a hydrogen atom or a linear or branched ($C_1$-$C_6$)alkyl group, wherein a compound of formula (Va):

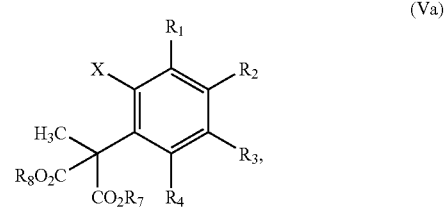

(Va)

wherein $R_1$, $R_2$, $R_3$, $R_4$, are as defined hereinbefore,
$R_7$ represents a linear or branched ($C_1$-$C_6$)alkyl group, $R_8$ represents a linear or branched ($C_1$-$C_6$)alkyl group, and X represents a halogen atom,
is converted into a compound of formula (IVa):

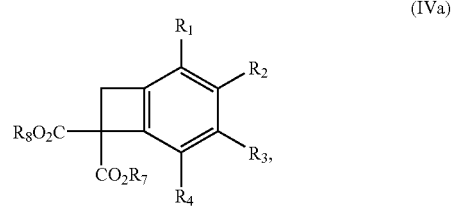

(IVa)

wherein $R_1$, $R_2$, $R_3$, $R_4$, $R_7$ and $R_8$ are as defined hereinbefore,
via a cyclisation reaction in the presence of a catalyst/ligand system comprising a palladium catalyst and an organic phosphine selected from tri-tert-butylphosphine, 2-biphenyl-di-tert-butylphosphine, 1,2,3,4,5-pentaphenyl-1'-(di-tert-butylphosphino)-ferrocene and tris(4-methoxy-2-methylphenyl)phosphine, or a phosphonium salt of the said phosphines, in the presence of a base, in an organic solvent,
and then the compound of formula (IVa) is converted into a compound of formula (VIa):

6. A process for the synthesis of ivabradine, pharmaceutically acceptable salts thereof, wherein a compound of formula (Vb):

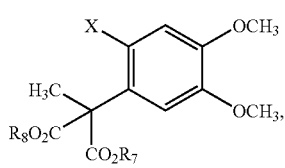
(Vb)

wherein $R_7$ represents a linear or branched ($C_1$-$C_6$)alkyl group, $R_8$ represents a linear or branched ($C_1$-$C_6$)alkyl group, and X represents a halogen atom, is converted into a compound of formula (VIIb):

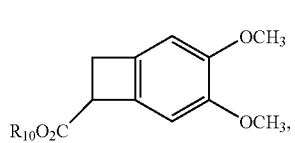
(VIIb)

wherein $R_{10}$ represents a hydrogen atom or a linear or branched ($C_1$-$C_6$)alkyl group, according to the process of claim 2 and then the compound of formula (VIIb) is converted into the compound of formula (VIII):

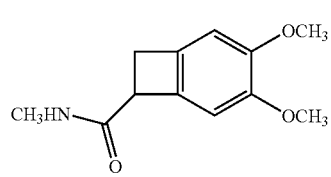
(VIII)

by reaction with methylamine, the reduction of which yields the compound of formula (III):

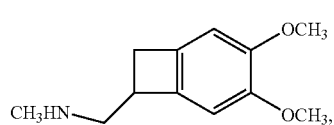
(III)

the resolution of which, in the presence of camphosulphonic acid, yields the compound of formula (II):

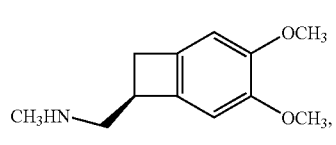
(II)

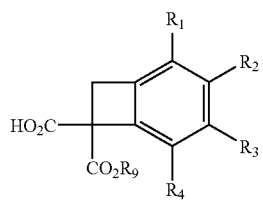
(VIa)

wherein $R_1$, $R_2$, $R_3$ and $R_4$ are as defined hereinbefore and $R_9$ is a linear or branched ($C_1$-$C_6$)alkyl group, by an ester saponification or hydrolysis reaction, and the compound of formula (VIa) is subjected to a decarboxylation reaction to yield the compound of formula (VIIa).

2. The process of claim 1, wherein the compound of formula (VIIa) is represented by formula (VIIb):

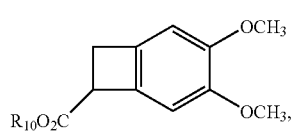
(VIIb)

wherein $R_{10}$ represents a hydrogen atom or a linear or branched ($C_1$-$C_6$)alkyl group.

3. The process of claim 1, wherein X represents a bromine atom.

4. A compound selected from those of formula (IVa):

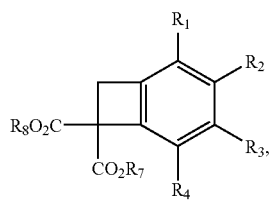
(IVa)

wherein $R_1$, $R_2$, $R_3$ and $R_4$, which may be identical or different, each represent a hydrogen atom, a linear or branched ($C_1$-$C_6$)alkyl group, a linear or branched ($C_1$-$C_6$)alkoxy group, a fluorine atom, a chlorine atom, a protected amine group, a protected hydroxyl group, an alkoxycarbonyl group in which the alkoxy group is linear or branched ($C_1$-$C_6$), or a $CF_3$ group, or $R_1$ and $R_4$ represent hydrogen and $R_2$ and $R_3$ together with the carbon atoms carrying them form a 1,3-dioxolane group, and $R_7$ and $R_8$, which may be identical or different, each represent a linear or branched ($C_1$-$C_6$)alkyl group.

5. A compound selected from those of formula (VIb):

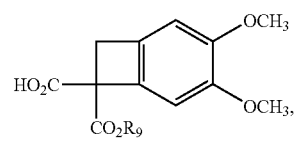
(VIb)

wherein $R_9$ is a linear or branched ($C_1$-$C_6$)alkyl group.

which is converted into ivabradine of formula (I):

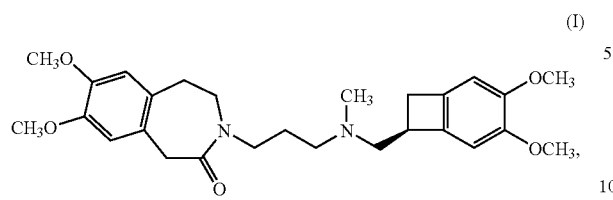

which may be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

7. The process of claim 6, wherein X represents a bromine atom.

* * * * *